United States Patent [19]

Brokken et al.

[11] Patent Number: 4,945,110
[45] Date of Patent: Jul. 31, 1990

[54] MEMBRAME-FORMING VETERINARY ANTIBACTERIAL TEAT DIP

[75] Inventors: Kyle Brokken, Chaska; Randolph S. Porubcan, Victoria, both of Minn.

[73] Assignee: Quali Tech, Inc., Chaska, Minn.

[21] Appl. No.: 339,197

[22] Filed: Apr. 14, 1989

Related U.S. Application Data

[63] Continuation-in-part of Ser. No. 62,278, Jun. 15, 1987, abandoned.

[51] Int. Cl.$^5$ .................. A61K 31/205; A61K 31/195; A61K 35/78
[52] U.S. Cl. .................................... 514/517; 514/568; 514/578; 514/782
[58] Field of Search ................ 514/568, 578, 517, 782

[56] References Cited

U.S. PATENT DOCUMENTS

| | | | |
|---|---|---|---|
| 1,691,228 | 11/1928 | Damiler et al. | 514/576 |
| 3,141,821 | 7/1964 | Compeau | 167/58 |
| 3,993,777 | 11/1976 | Caughman et al. | 424/329 |
| 4,012,504 | 3/1977 | Eckols | 424/150 |
| 4,017,408 | 4/1977 | Fults | 252/106 |
| 4,025,628 | 5/1977 | Dewey et al. | 424/249 |
| 4,049,830 | 9/1977 | Pugliese | 424/343 |
| 4,067,997 | 1/1978 | Kabara | 424/312 |
| 4,113,854 | 9/1978 | Andrews et al. | 424/81 |
| 4,199,564 | 4/1980 | Silver et al. | 424/80 |
| 4,199,602 | 4/1980 | Lentsch | 424/343 |
| 4,258,056 | 3/1981 | Lentsch | 424/303 |
| 4,271,149 | 6/1981 | Winicov et al. | 424/150 |
| 4,311,709 | 1/1982 | Dybas et al. | 424/330 |
| 4,344,967 | 8/1982 | Easton et al. | 424/359 |
| 4,376,787 | 3/1983 | Lentsch et al. | 424/315 |
| 4,401,666 | 8/1983 | Wedig et al. | 424/245 |
| 4,434,181 | 2/1984 | Marks et al. | 424/326 |
| 4,446,153 | 5/1984 | Yang | 424/343 |
| 4,525,351 | 6/1985 | Gehrman et al. | 424/95 |
| 4,542,125 | 9/1985 | Gorman et al. | 514/57 |
| 4,584,192 | 4/1986 | Dell et al. | 424/81 |
| 4,610,993 | 9/1986 | Wedig et al. | 514/335 |

FOREIGN PATENT DOCUMENTS 1525441 9/1978 United Kingdom .

OTHER PUBLICATIONS

Remington's Pharmceutical Sciences, 14th Ed. (1970), pp. 793, 1189.
Miller, et al., Encyclopedia of Animal Care, 6th Ed. (1962), pp. 214–215.
Block, Disinfection, Sterilization and Preservation, 2d Ed. 319-324 (1977).
Philpot, et al., J. Dairy Sci., 61(7); pp. 956–963 (1978).

Primary Examiner—Mukund J. Shah
Assistant Examiner—E. C. Ward
Attorney, Agent, or Firm—Faegre & Benson

[57] ABSTRACT

A veterinary antibacterial composition is described which is viscosity stabilized, aqueous, topically adherent and forms a relatively tough, self-supporting film that adheres to the animal until removed by water washing. The composition is an aqueous solution of:
an aliphatic sulfate or sulfonate salt detergent;
lactic acid or a food grade salt thereof;
a bactericidal food grade organic acid selected from benzoic acid, sorbic acid, citric acid and lower alkanoic acids, and food grade salts thereof;
a veterinarily acceptable food grade pectin or gum; and
a veterinarily acceptable water soluble emollient selected from short chain aliphatic polyols of up to six carbon atoms;

The composition is suitable, for example, as a teat dip and bacterial control approaching 100% is demonstrated by in vitro and in vivo testing.

35 Claims, No Drawings

MEMBRAME-FORMING VETERINARY ANTIBACTERIAL TEAT DIP

CROSS REFERENCE TO RELATED APPLICATION

This application is a continuation-in-part of our co-pending application Ser. No. 062,278, filed June 15, 1987, now abandoned.

FIELD OF THE INVENTION

This invention provides a relatively tough, self-supporting topically adherent film-forming veterinary antibacterial composition. When applied topically to animals, this film-forming antibacterial composition rapidly dries to a relatively tough yet flexible, self-supporting adherent protective antibacterial barrier film, which adheres to the animal until removed by water washing. The present composition is especially suitable for topical application to dairy animals as a teat dip for the prevention and control of bovine mammary infections and inflammations. The present composition is particularly desirable, since it is comprised of innocuous, environmentally benign components which do not present any problem of irritation either to animals or to persons who come in contact with it and also do not present any problem of residual contamination to the animals' milk supply.

RELATED BACKGROUND INFORMATION

The fact that the present composition forms a RELATIVELY TOUGH, SELF-SUPPORTING TOPICALLY ADHERENT ANTIBACTERIAL FILM ON THE ANIMAL is a particularly novel and unobvious feature of the present invention and is completely unsuggested by prior available veterinary topical antibacterials and teat dips. Many prior patents, as discussed herein below, have interpreted the formation of a gummy, sticky surface residue on the animal as a membrane. By contrast, the protective membrane formed by the present composition is a relatively tough, self-supporting membrane which, under actual field use conditions, can be peeled away from the animal as a self-supporting membrane similar to a sheet of polyplastic.

Certain other patents (as described herein below) have disclosed the use of latex to form a protective barrier in topical antibacterials. However, such latex-based compositions must be manually peeled from the animal at removal time. Also, latex-based teat dips leave non-water soluble latex residues which clog the in-line filters of milk collecting equipment. By contrast, the protective membrane formed by the present composition, while being relatively tough and self-supporting, is also easily and completely removed from the animal by simple water washing.

These film-forming advantages, as well as other novel and unobvious advantages of the present topical antibacterial, will be described in greater detail further herein.

Animals are known to be particularly susceptible to various topical bacterial infections and inflammations due to the high bacterial count of their environments. Ruminant dairy animals are especially susceptible to infections and inflammations of the udder, known as bovine mastitis, in intensive milk producing operations. Effective application of antibacterial formulations to animals requires that the formulation remain adherently in contact with the affected area. Antibacterial teat dip application is an important regimen in effective dairy herd management, and it is recognized that a teat dip's effectiveness requires that it remain in contact with the animals' teats and udders between milkings, but be readily and completely removable by simple washing at the next milking time.

A variety of topical veterinary antibacterials, including those for teat dip applications are known, as described in some of the following United States patents. U.S. Pat. No. 4,012,504 describes a solution of iodine in mineral oil. U.S. Pat. No. 4,017,408 describes a water soluble liquid concentrate of iodine, dimethyl sulfoxide and a liquid detergent. U.S. Pat. No. 4,271,149 describes iodine-containing compositions in which iodine levels are maintained by the presence of iodide and iodate. U.S. Pat. No. 4,049,830 describes a pH controlled oil-in-water teat dip including bronopol and certain lipids. U.S. Pat. No. 4,199,602 describes neutral to mildly acidic teat dips based on anti-microbial nitroalkanols potentiated with an aminocarboxylic-type chelating agent.

U.S. Pat. No. 4,258,056 describes teat dips similar to those of U.S. Pat. No. 4,199,602 and including an anionic surfactant. U.S. Pat. No. 4,434,181 describes a composition comprising a cellulosic water soluble film former and chlorhexidine in a freeze-resistant volatile solvent. U.S. Pat. No. 3,993,777 utilizes quaternary annonium surfactant germicides in conjunction with certain emollients. U.S. Pat. No. 4,376,787 uses acidic pH controlled anionic surfactant compositions.

U.S. Pat. No. 4,199,564 describes an aqueous tincture of a lower alkanol microbicide, a film-forming polymer and an emollient. U.S. Pat. No. 4,446,153 describes a composition of a phenyl alkanol, a surfactant emulsifier and an optional emollient, controlled to a normal to mildly acidic pH. U.S. Pat. No. 4,401,666 describes a teat dip using a metallic salt of pyridine-2-thione-N-oxide. U.S. Pat. No. 4,610,993 describes a teat dip using 2,2'-dithiobis-pyridine 1,1'-dioxide and adducts thereof. U.S. Pat. No. 4,067,997 discloses certain phenolic compounds, such as resorcinol compounds, to be the antimicrobicide in a claimed synergistic combination with a non-ionic surfactant and a polyol.

A chlorinated cyanurate provides the active ingredient in the powdered, water-dispersible formulation of U.S. Pat. No. 4,025,628. A bis[4-(amino)-1-pyridinium]alkane salt is the antimicrobial agent in the teat dips of U.S. Pat. No. 4,542,125. In the teat dips of U.S. Pat. No. 4,311,709, the antimicrobially active ingredient is a loweralkyl substituted diphenyl polyamine.

Prophylactic treatment of mastitis is taught by the use of film-forming teat coating dips which physically entrap the bacteria, as in U.S. Pat. No. 4,113,854 (an aqueous medium containing a polymer latex and a water soluble polymer thickening agent), U.S. Pat. No. 4,344,967 (an aqueous solution of a protein hydrolystate, glycerol and optionally a water-miscible solvent), and U.S. Pat. No. 4,584,192 (a copolymer of certain monomeric substituted acrylic acid esters with N-vinyl lactam). It is often suggested to include antimicrobials in these compositions to achieve maximum effectiveness.

It has recently been found to be important to avoid the use of antibiotics, such as those generally used in the above mentioned veterinary antibacterials and teat dips, for a number of reasons. Continual use of such products can result in the antibiotics accumulating in the animals' milk supply to a level where they become a source of contamination, rendering the milk unfit for human consumption. Also, the excessive use of antibiotics in veterinary medicine apparently contributes to the development of resistant strains of bacteria, which may be a source of both animal and human diseases.

Accordingly, it has been considered desirable in veterinary use, especially in the dairy industry, to develop an effective antibacterial and teat dip which avoids the use of conventional antibiotics. Thus, in U.S. Pat. No. 4,545,351, a liquid adherent teat dip composition is provided which avoids the use of such conventional antibiotics, comprising an aqueous acidic suspension of a coagulated casein, solubilized by an aliphatic sulfate detergent and optionally glycerin and lactobacillus-elaborated antibiotic-like factors.

It is further important that a veterinary topical antibacterial and teat dip be available that is comprised of ingredients which are food grade, innocuous and non-irritating as possible to both the animals and the humans who come in contact with it, while also maintaining a high level of antimicrobia effectiveness in the prevention, control and treatment of bovine mastitis. It is particularly important that a teat dip be available which is effective against gram negative bacterial pathogens, such as *Escherichia coli*, which are a primary source of veterinary infections such as bovine mastitis. Most teat dips currently available are not effective against gram negative bacterial pathogens. Additionally, an effective teat dip should satisfy the other criteria previously described above.

SUMMARY OF THE INVENTION

It has now been discovered that an extremely effective, viscosity stabilized, aqueous, topically adherent, film-forming veterinary antibacterial composition, which admirably satisfies the selection criteria outlined above for veterinary antibacterial and teat dip compositions, can be prepared from ingredients which are highly innocuous and non-irritating to both animals and to humans. This composition is especially valuable for application to dairy animals as a mastitis-controlling teat dip. The composition of this invention is an aqueous solution comprising:

an aliphatic sulfate or sulfonate salt detergent in an amount between about 4 to 8 weight percent of the total composition;

lactic acid, a food grade salt thereof, or admixtures thereof in an amount between 0.01 to 10 weight percent of the total composition;

a bactericidal food grade organic acid, a food grade salt thereof or admixtures thereof, wherein the bactericidal food grade organic acid is selected from benzoic acid, sorbic acid, citric acid, and lower alkanoic acids;

a veterinarily acceptable food grade pectin or gum in an amount between about 0.02 to 2.5 weight percent of the total composition; and a veterinarily acceptable water soluble emollient selected from short chain aliphatic polyols of up to six carbon atoms.

This composition is viscosity stabilized between 80 to 160 cps at 25 degrees C. and forms a topically adherent flexible protective antibacterial barrier film which adheres to the animal until removed by water washing. Additionally, if desired, certain other veterinarily acceptable ingredients may be incorporated into the present formulation. For example, a defoamer and a dye may be added and other additional disinfecting and antimicrobial substances may be added.

This formulation provides a gentle acting solution for topical veterinary application to prophylactically control infection-causing bacteria, including those associated with bovine mastitis. When topically applied, the solution dries in a short period of time to an adherent flexible protective antibacterial barrier film which adheres to the animal until removed by washing with water. When used as a teat dip treatment, the solution dries on the animals' teats and udders in a short period of time to a flexible protective antibacterial barrier film which adheres to the animal and which is readily and completely removable at the next milking or treatment time by water washing.

DETAILED DESCRIPTION OF THE INVENTION

In preparing the compositions of this invention, the aliphatic sulfate or sulfonate salt detergent may be sodium, potassium or ammonium aliphatic sulfates or sulfonates, or mixtures thereof, containing from 10 to 18 carbons in their aliphatic groups. The preferred detergents are the aliphatic sulfates which are composed primarily of dodecyl sulfate (C12 aliphatic group), such as sodium lauryl sulfate. Lesser amounts of C14 and C16 aliphatic sulfates may be present in admixture with the dodecyl sulfate. A sufficient amount of aliphatic sulfate or sulfonate salt detergent should be used so that it provides an effective solubilizing effect in the final aqueous composition. For example, the selected amount of aliphatic sulfate or sulfonate salt detergent may be within the range of 0.0580 to 10.0000 percent by weight of the total composition, preferably from about 4 to 8 weight percent of the total composition.

Lactic acid or its food grade salts or mixtures thereof are present in the composition to provide a bacteriostatic effect by lowering the acidity of the composition to a pH at which bacterial pathogens will be unable to reproduce and grow, that is a pH of about 4 or below. Thus, lactic acid, its food-grade salts or mixtures thereof are present in the composition in an amount to lower the pH below 4, preferably to within the range of 2.85 to 3.00. To achieve this level of acidity, lactic acid, its food-grade salts or mixtures thereof are present in the composition in an amount between about 0.01 to 10.00 percent by weight of the total composition, preferably from about 0.80 to 1.20 percent by weight.

The bactericidal food-grade organic acid or its food grade salts or mixtures thereof used in the present composition are selected from food-grade organic acids and the food-grade salts thereof which provide broad spectrum antibacterial action. Suitable organic acids include benzoic acid, sorbic acid, citric acid, lower alkanoic acids and their food-grade salts, such as the sodium, potassium or ammonium salts thereof. These organic acids, their salts, or mixtures thereof are present in the composition in an amount between about 0.0010 to 0.1000 percent by weight, preferably from 0.0050 to 0.150 percent by weight. The presently preferred organic acids are benzoic acid and sorbic acid, with benzoic acid suitably present as sodium benzoate and sorbic acid suitably present as the free acid. Each of these acids, or their salts, are present in the composition in equal amounts, that is, they each are present in the composition in an amount between about 0.0005 to 0.0500 percent by weight, preferably from about 0.0025 to 0.0075 percent by weight.

The pectin or gum component of the present novel composition may be any food grade natural or synthetic pectin or gum which will impart to the final composition a viscosity of at least 80 centipoise. Suitable natural pectins include apple pectin and citrus pectin. Suitable gums may also include guar gum or carageenan. Presently preferred is citrus pectin gum, derived from citrus peel. It consists of partially methoxylated polygalacturonic acid. A suitable citrus pectin for use in the present formulation is available from Hercules, Inc., Wilmington, Del., under the name HM DD SLOW-SET Genu Pectin. The pectin or gum is present in the formulation in an mount sufficient to impart to the final composition a viscosity of at least 80 centipoise, for example, between 80 to 300 centipoise, preferably between 80 to 160 centipoise at 25 degrees C. Thus, the pectin or gum is present in the composition in an amount between about 0.02 to 2.50 percent by weight, preferably from about 1.50 to 2.50 percent by weight.

The water-soluble veterinarily acceptable emollient may be a short chain aliphatic polyol of up to 6 carbon atoms or mixtures thereof. Examples of suitable emollients for use in the present formulation are propylene glycol, ethylene glycol, glycerin and sorbitol. The emollient is present in the composition in an amount between about 2.50 to 10.00 percent by weight. The presently preferred emollients are glycerin, propylene glycol or ethylene glycol.

Other selected ingredients may also be added to the present novel formulation to impart special desired qualities thereto. For example, a veterinarily acceptable defoamer may be added to prevent excessive foaming of the teat dip due to the presence of the aliphatic sulfate or sulfonate salt detergent. A particularly acceptable defoamer has been found to be a food grade silicone defoamer emulsion, such as Mazu DF 200S available from Mazer Chemicals, Inc., Gurnee, Ill.

In order to render the composition readily visible for inspection purposes on the animals, a dye or colorant that is considered generally acceptable for veterinary and food use may be added. This allows the animal herdsmen to readily observe that all animals have been treated with the veterinary antibacterial of this invention, for example, when used as a teat dip, after each milking or treatment operation and also to determine that the product has been thoroughly and completely washed from the animals prior to the next milking or treatment operation. FD & C Blue #1 has been found to be an acceptable colorant. In addition, any other suitable food-grade antimicrobials, antibacterials or disinfectants may suitably be added to the final composition if desired.

A final important component of the present teat dip formulation is water, preferably deionized water, which is present in an amount between about 30 to 90 percent by weight of the total composition, preferably from about 75 to 85 percent by weight.

All of the ingredients used in formulating the present antibacterial composition are safe, innocuous and non-irritating to both humans and animals when used in the manner intended as described herein. All of the ingredients are listed on the Food and Drug Administration GRAS (generally regarded as safe) list. The aliphatic sulfate and sulfonate salt detergents are safe, innocuous and non-irritating when used topically by both humans and animals, and are commonly found in a variety of topical cleansing agents formulated for human and for veterinary use.

Thus, in preparing the present novel composition, the antibacterially active ingredients comprise the aliphatic sulfate or sulfonate salt detergent, the bactericidal food grade organic acid and lactic acid. These ingredients are present in the total composition in an amount between about 0.07 to 16.00 weight percent of the total composition, generally between about 1.20 to 5.00, preferably about 3.00 weight percent of the total composition.

In a preferred method of preparing the compositions of this invention, the bactericidal food-grade organic acid, its salts or mixture thereof are admixed with a minor portion of the required amount of deionized water. Also, the desired visibly observable colorant may now be added. Slight warming of this solution above room temperature may be required in order to assure formation of an even solution.

In a separate mixing vessel, the citrus pectin is slowly added to the remaining major portion of water for the formulation with adequate agitation to assure complete dissolution. Again, slight warming above room temperature may be required to assure formation of an even and complete solution of the pectin or gum. A minor amount of sodium bicarbonate may be added with the citrus pectin for quick dispersion. When the pectin or gum is completely in solution, the aliphatic sulfate or sulfonate salt detergent and lactic acid or its salts are added, along with the defoamer, if desired. After this solution is complete the solution of the bactericidal food grade organic acid is added thereto, along with the emollient and any other additives which may be desired. Mixing is continued for a time until an even, homogeneous solution has been obtained, for example, up to about half an hour or more if required.

At the completion of formation of the present novel formulation, the pH will be in the relatively acidic range below about 4, generally between 2.85–3.00, and the viscosity will be above 80 centipoise, generally between about 80 to 300 centipoise, preferably between about 90 and 160 centipoise.

The resulting compositions are useful for topical application to animals, and in particular are useful in the prevention, control and prophylaxis of bovine mastitis, especially when applied as a teat dip. When applied to the animals' teats and udder quarters, some but not all of the water will evaporate from the composition, leaving a residual adherent flexible film that maintains the present antibacterial composition in contact with the animals' teats and udders, while at the same time sealing them against the introduction of further bacterial infection. Such contact will be maintained until the next milking or treatment time, when the teat dip can be readily removed by simple thorough washing with water. The presence of an emollient in the present composition further serves to maintain the condition of the animals teats and udder quarters. The present topical antibacterial is suitable for application to animals over a wide temperature range, for example, between 35°–105° F. and the preferred range for application is 55°–95° F.

When the composition is prepared as hereinabove described, it is not necessary to discard the treated animals milk supply for up to 3 to 4 days, as is sometimes necessary with other teat dip formulations containing antibiotics or other ingredients which render the milk unfit for consumption.

The compositions of this invention may also be used for other topical veterinary antimicrobial applications. For example, the compositions can be used as a foot dip, especially with livestock raised under crowded feed lot conditions. Other types of wounds or sores on livestock and domestic animals are also susceptible to treatment with the present compositions.

If desired, the present composition as herein described may be diluted up to a total of 50 percent by volume with water with no significant loss of the antibacterial effectiveness. It should be noted that dilution of the present composition with water will be accompanied by a decrease of its film forming properties, and that at the maximum dilution of 50 percent by volume its film forming properties are essentially absent.

The following examples are presented to illustrate the preparation and testing of the present novel compositions.

EXAMPLE I

A 1,000 pound batch of the composition of this invention is prepared as follows.

Solution A

| | |
|---|---|
| Sodium benzoate | 0.0500 pounds |
| Sorbic acid | 0.0500 pounds |
| FD&C Blue #1 | 0.0602 pounds |

These ingredients are admixed with approximately 3% of the total water required for the batch in a stainless steel vessel.

Solution B

| | |
|---|---|
| Citrus pectin | 18.0000 pounds |
| Sodium lauryl sulfate (29 wt % aqueous solution) | 172.4140 pounds |
| Lactic acid (88 wt % aqueous solution) | 10.0000 pounds |

These ingredients are admixed with the rest of the water needed to make up the total amount of 749.4258 pounds of water in the entire batch.

Solution A is then added to Solution B, along with 50.000 pounds of glycerin. Mixing is continued to obtain an even, homogeneous solution.

EXAMPLE II

The composition prepared according to Example I has the following physical characteristics:

| | |
|---|---|
| Color: | Blue |
| Odor: | Fresh detergent odor |
| Viscosity @ 25 degrees C: | 160 centipoise |
| Antimicrobial Activity: | 10 microliters of the composition of Example I shows total contact kill power against S. aureus and E. coli on a streaked SMA culture plate. |
| Homogeneity: | The composition of Example I is homogeneous with no lumps or foreign matter. |

EXAMPLE III

This Example is presented to demonstrate that the formation of the membrane by the composition of this invention is a function of having the pectin or gum interacting with the emollient and the aliphatic sulfate or sulfonate detergent in a synergistic fashion.

Five alternative samples were prepared based on the formulation set forth in Example I as follows:

1. Formulation of Example I without citrus pectin.
2. Formulation of Example I without glycerin.
3. Formulation of Example I without sodium lauryl sulfate.
4. Formulation of Example I without glycerin and sodium lauryl sulfate.
5. Formulation of Example I.

Test 10 ml samples of each of these formulations were placed in separate evaporation dishes and exposed to microwave heating for 1.0 minute at the "high setting" on a Whirlpool model RFM2800P microwave oven (650 watt output). Each formulation was treated separately in the microwave oven and was positioned in the geometric center of the oven. After microwave heating, the samples were cooled for one hour at room temperature and the quality of any membrane which formed was immediately evaluated.

Results

1. No membrane formed.
2. Poor quality membrane; crumbly, imperfect.
3. No membrane, only a pool of gummy syrup.
4. No membrane; only a pool of gummy syrup.
5. Excellent membrane; it peels away from dish and stays together as a perfect sheet—like a polyplastic sheet. This membrane dissolves in warm water.

The microwave was used in this Example solely for the purpose of speeding up the observability of the formation of the membrane by the present novel formulation. Similar tests under normal room temperature conditions result in the same formation of membrane over a slightly longer period of time.

EXAMPLE IV

Using the composition of this invention prepared as described in Example I, field testing of this composition for use as a teat dip was carried out according to the following procedures.

Five dairy cows, selected for normal teat size and structure, were used in the test. Each cow was challenged with $5 \times 10^7$ colony forming units (CFU)/ml E. coli solution. The bacterial challenge solution was allowed to dry on the teats for 10 minutes. The teat was then dipped in a solution of the composition of this invention as described in Example I. The teat dip of Example I dried to a topically adherent film. This teat dip of Example I was allowed to remain on the teats for 30 minutes and the teats were washed with neutralizing buffer, removing all of the teat dip. The buffer solution was then plated onto blood agar media and incubated for 24 hours at 37 degrees C. The plate counts were then completed.

This procedure was completed on five cows for four days. The average percent reduction of the bacterial count was 99.95%. These excellent results compare well to currently available teat dips using harsh germicidal ingredients such as iodine, but are safe and gentle and do not present any problem of irritation to either animals or persons who come in contact with it or of contamination of the animals' milk supply.

EXAMPLE V

Using the composition of this invention prepared as described in Example I, field testing of this composition for use as a teat dip was carried out according to the procedures as described above in Example IV.

The average percent reduction of the bacterial count was 99.99%. These excellent results also compare well to currently available teat dips using harsh germicidal ingredients such as iodine, but are safe and gentle and do not present any problem of irritation to either animals or persons who come in contact with it or of contamination of the animals milk supply.

What is claimed is:

1. A viscosity stabilized, aqueous, topically adherent, self-supporting film-forming veterinary antibacterial composition comprising:
    an aliphatic sulfate or sulfonate salt detergent in an amount between about 4 to 8 weight percent of the total composition;
    lactic acid, a food grade salt thereof, or admixtures thereof in an amount between 0.01 to 10 weight percent of the total composition;
    a bactericidal food grade organic acid selected from benzoic acid, sorbic acid, citric acid, lower alkanoic acids, a food grade salt thereof, or admixtures thereof in an amount between 0.001 to 0.100 weight percent of the total composition;
    a film forming food grade pectin or gum in an amount between about 0.02 to 2.5 weight percent of the total composition; and
    a veterinarily acceptable water soluble emollient selected from short chain aliphatic polyols of up to six carbon atoms;
having a viscosity stabilized between 80 to 160 cps at 25 degrees C. and forming a topically adherent flexible protective antibacterial barrier film which adheres to the animal until removed by water washing.

2. A composition of claim 1, wherein the aliphatic sulfate or sulfonate salt detergent is selected from sodium, potassium and ammonium aliphatic sulfates and sulfonates and mixtures thereof, containing from 10 to 18 carbons in their aliphatic groups.

3. The composition of claim 2, wherein the aliphatic sulfate salt detergent is dodecyl sulfate salt.

4. The composition of claim 3, wherein the dodecyl sulfate salt detergent is sodium lauryl sulfate.

5. The composition of claim 1, wherein the bactericidal food grade organic acid comprises a mixture of sorbic acid and sodium benzoate.

6. The composition of claim 1, wherein the film forming food grade pectin or gum is selected from citrus pectin, apple pectin, guar gum and carageenan.

7. The composition of claim 6, wherein the citrus pectin is a purified water-soluble natural gum, derived from citrus peel, consisting of partially methoxylated polygalacturonic acid.

8. The composition of claim 7, wherein the citrus pectin additionally contains sodium bicarbonate in minor amount to facilitate the dissolution of the citrus pectin.

9. The composition of claim 1, containing additional veterinarily acceptable ingredients selected from defoamers, dyes, additional antimicrobials, and mixtures thereof.

10. The composition of claim 1, wherein the emollient is selected from glycerin, propylene glycol, sorbitol, ethylene glycol and mixtures thereof.

11. The composition of claim 10, where the emollient is glycerin.

12. The composition of claim 9, wherein the aliphatic sulfate or sulfonate salt detergent is sodium lauryl sulfate, the antibacterially active food grade organic acid is a mixture of sodium benzoate and sorbic acid and the additional veterinarily acceptable ingredients include, a defoamer and a dye.

13. The composition of claim 9, wherein the aliphatic sulfate or sulfonate salt detergent is sodium lauryl sulfate, the antibacterially active food grade organic acid is a mixture of sodium benzoate and sorbic acid, the emollient is glycerin, and the additional veterinarily acceptable ingredients include a defoamer and a dye.

14. A method of preparing a viscosity stabilized, aqueous, topically adherent, film-forming veterinary antibacterial composition according to claim 1, comprising the steps of:
    (1) preparing an aqueous solution of the bactericidal food grade organic acid, its food grade salts or mixtures thereof;
    (2) preparing an aqueous solution of the film forming food grade pectin or gum, the aliphatic sulfate or sulfonate detergent and lactic acid;
    (3) adding the solution of step (1) to the solution of step (2) with thorough mixing; and
    (4) adding a veterinarily acceptable water soluble emollient to the solution of step (3) with thorough mixing.

15. The method of claim 14, wherein the bactericidal food grade organic acid comprises a mixture of sorbic acid and sodium benzoate.

16. The method of claim 14, wherein the film forming food grade pectin or gum is citrus pectin or apple pectin.

17. The method of claim 15, wherein the citrus pectin is purified water-soluble natural gum, derived from citrus peel, consisting of partially methoxylated polygalacturonic acid.

18. The method of claim 17, wherein the citrus pectin additionally contains sodium bicarbonate in a minor amount to facilitate the dissolution of the citrus pectin.

19. The method of claim 14, wherein the solution of step (1) additionally comprises veterinarily acceptable ingredients selected from dye and additional antimicrobials.

20. The method of claim 14, wherein the solution of step (2) additionally comprises a veterinarily acceptable defoamer.

21. The method of claim 14, wherein the emollient is selected from glycerin, propylene glycol, sorbitol, ethylene glycol and mixtures thereof.

22. The method of claim 21 wherein the emollient is glycerin.

23. The method of using the composition of claim 1 as a topical veterinary antibacterial composition comprising administering an antibacterially effective amount of the composition topically to animals and allowing the composition to dry to a topically adherent flexible protective film-forming antibacterial barrier.

24. The method of using the composition of claim 1 for control of bovine mastitis comprising applying an antibacterially effective amount of the composition of claim 1 to the teats and udder quarters of bovine animals and allowing the composition to dry to a topically adherent flexible protective film-forming antibacterial barrier.

25. The method of using the composition of claim 13 for the control of bovine mastitis comprising applying an antibacterially effective amount of the composition to the teats and udder quarters of bovine animals and allowing the composition to dry to a topically adherent flexible protective film-forming antibacterial barrier.

26. The method of using the composition of claim 13 as a topical veterinary antibacterial composition comprising administering an antibacterially effective amount of the composition topically to animals and allowing the composition to dry to a topically adherent flexible protective film-forming antibacterial barrier.

27. A viscosity stabilized, aqueous, topically adherent, self-supporting film-forming veterinary antibacterial composition comprising:
   sodium lauryl sulfate in amount between about 4 to 8 weight percent of the total composition;
   lactic acid, a food grade salt thereof, or admixtures thereof in an amount between 0.01 to 10 weight percent of the total composition;
   a bactericidal food grade organic acid selected from benzoic acid, sorbic acid, citric acid, lower alkanoic acids, a food grade salt thereof, or admixtures thereof in an amount between 0.001 to 0.100 weight percent of the total composition;
   a film forming food grade pectin or gum in an amount between about 0.02 to 2.5 weight percent of the total composition; and
   a veterinarily acceptable water soluble emollient selected from short chain aliphatic polyols of up to six carbon atoms;
having a viscosity stabilized between 80 to 160 cps at 25 degrees C. and forming a topically adherent flexible protective antibacterial barrier film which adheres to the animal until removed by water washing.

28. A viscosity stabilized, aqueous, topically adherent, self-supporting film-forming veterinary antibacterial composition comprising:
   an aliphatic sulfate of sulfonate salt detergent in an amount between about 4 to 8 weight percent of the total composition;
   lactic acid, a food grate salt thereof, or admixtures thereof in an amount between 0.01 to 10 weight percent of the total composition;
   a mixture of sorbic acid and sodium benzoate present in an amount between 0.001 to 0.100 weight percent of the total composition;
   a film forming food grade pectin or gum in an amount between about 0.02 to 2.5 weight percent of the total composition; and
   a veterinarily acceptable water soluble emollient selected from short chain aliphatic polyols of up to six carbon atoms;
having a viscosity stabilized between 80 to 160 cps at 25 degrees C. and forming a topically adherent flexible protective antibacterial barrier film which adheres to the animal until removed by water washing.

29. A viscosity stabilized, aqueous, topically adherent, self-supporting film-forming veterinary antibacterial composition comprising:
   sodium lauryl sulfate in an amount between about 4 to 8 weight percent of the total composition;
   lactic acid, a food grade salt thereof, or admixtures thereof in an amount between 0.01 to 10 weight percent of the total composition;
   a mixture of sorbic acid and sodium benzoate present in an amount between 0.001 to 0.100 weight percent of the total composition;
   a film forming food grade pectin or gum in an amount between about 0.02 to 2.5 weight percent of the total composition;
   a veterinarily acceptable water soluble emollient selected from short chain aliphatic polyols of up to six carbon atoms;
having a viscosity stabilized between 80 to 160 cps at 25 degrees C. and forming a topically adherent flexible protective antibacterial barrier film which adheres to the animal until removed by water washing.

30. The composition of claim 29, containing additional veterinarily acceptable ingredients selected from defoamers, dyes, additional antimicrobials, and mixtures thereof. m 31. The composition of claim 30, wherein the additional veterinarily acceptable ingredients include, a defoamer and a dye.

32. The composition of claim 31, wherein the emollient is glycerin.

33. A method of preparing a viscosity stabilized, aqueous, topically adherent, film-forming veterinary antibacterial composition according to claim 28, comprising the steps of:
   (1) preparing an aqueous solution of the mixture of sorbic acid and sodium benzoate;
   (2) preparing an aqueous solution of the bactericidal food grade organic acid, its food grade salts or mixtures thereof;
   (3) adding the solution of step (1) to the solution of step (2) with thorough mixing; and
   (4) adding a veterinarily acceptable water soluble emollient to the solution of step (3) with thorough mixing.

34. The method of claim 33, wherein the citrus pectin is purified water-soluble natural gum, derived from citrus peel, consisting of partially methoxylated polygalacturonic acid.

35. The method of claim 34, wherein the citrus pectin additionally contains sodium bicarbonate in a minor amount to facilitate the dissolution of the citrus pectin.

* * * * *